United States Patent
Shimozato et al.

(10) Patent No.: US 9,918,632 B2
(45) Date of Patent: Mar. 20, 2018

(54) OPHTHALMOLOGIC APPARATUS AND CONTROL METHOD THEREOF

(71) Applicant: CANON KABUSHIKI KAISHA, Tokyo (JP)

(72) Inventors: Yuki Shimozato, Kawasaki (JP); Wataru Sakagawa, Yokohama (JP); Toshifumi Masaki, Tokyo (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 50 days.

(21) Appl. No.: 14/681,461

(22) Filed: Apr. 8, 2015

(65) Prior Publication Data

US 2015/0297077 A1    Oct. 22, 2015

(30) Foreign Application Priority Data

Apr. 16, 2014    (JP) ................. 2014-084373

(51) Int. Cl.
*A61B 3/14*    (2006.01)
*A61B 3/10*    (2006.01)
*A61B 3/12*    (2006.01)

(52) U.S. Cl.
CPC ............... *A61B 3/14* (2013.01); *A61B 3/102* (2013.01); *A61B 3/1225* (2013.01)

(58) Field of Classification Search
CPC ......... A61B 3/14; A61B 3/102; A61B 3/1225; H04N 5/04
USPC ................................................ 351/206, 208
See application file for complete search history.

(56) References Cited

U.S. PATENT DOCUMENTS

| | | |
|---|---|---|
| 5,822,034 A | 10/1998 | Shimashita et al. |
| 8,425,038 B2 | 4/2013 | Masaki |
| 8,789,948 B2 | 7/2014 | Masaki |
| 8,804,127 B2 | 8/2014 | Shimoyama et al. |
| 8,960,904 B2 | 2/2015 | Aoki et al. |
| 8,960,905 B2 | 2/2015 | Aoki et al. |
| 8,970,849 B2 | 3/2015 | Sakagawa et al. |
| 9,022,569 B2 | 5/2015 | Nakahara et al. |
| 2013/0195337 A1 | 8/2013 | Sakagawa |
| 2014/0257076 A1 | 9/2014 | Shimozato |
| 2014/0316232 A1 | 10/2014 | Shimozato |

FOREIGN PATENT DOCUMENTS

JP    2012-213490 A    11/2012

*Primary Examiner* — Jack Dinh
(74) *Attorney, Agent, or Firm* — Fitzpatrick, Cella, Harper & Scinto

(57) ABSTRACT

The present invention reduces a positional displacement of an acquired image attributable to a delay from the issuance of a drive instruction to a scanner to the scanner actually reaching an instructed drive position. An ophthalmologic apparatus has a light scanning unit which scans measuring light on an eye to be examined, an acquisition unit which receives light reflected from the eye to be examined and acquires a light receiving signal, and an instruction unit which instructs the drive position of the light scanning unit. The apparatus further includes a position detection unit which detects the current position of the light scanning unit and a measurement unit which measures the drive time delay from the issuance of an instruction by the instruction until the current position reaches the instructed drive position. The acquisition unit starts acquiring the light receiving signal at timing based on the drive time delay.

12 Claims, 11 Drawing Sheets

DESIRED IMAGE          ACQUIRED IMAGE

DESIRED IMAGE

OPHTHALMOLOGIC APPARATUS AND CONTROL METHOD THEREOF

BACKGROUND OF THE INVENTION

Field of the Invention

The present invention relates to an ophthalmologic apparatus adapted to scan measuring light on the fundus or the anterior ocular segment of an eye to be examined and to image the fondue or the anterior ocular segment, and a control method of the ophthalmologic apparatus.

Description of the Related Art

Among a variety of ophthalmologic apparatuses using optical apparatuses currently in use, an optical coherence tomography apparatus (hereinafter referred to as "the OCT" or "the OCT apparatus") and a scanning laser ophthalmoscope (hereinafter referred to as "the SLO" or "the SLO apparatus") have been known. These apparatuses are capable of acquiring the images of a fundus or an anterior ocular segment with a high resolution by scanning measuring light on the fundus or the anterior ocular segment of an eye to be examined and by imaging the light reflected from the eye to be examined. This is making these apparatuses indispensable as ophthalmologic apparatuses.

The OCT apparatus and the SLO apparatus use a galvano scanner or like as a means for scanning measuring light. The galvano scanner is constituted of a mirror fixed to a rotating shaft, an actuator that rotatively drives the rotating shaft, and a driver that drives the actuator. To drive the scanner, an instructed drive position is given to the driver. As an image acquiring means, an avalanche photo diode (hereinafter referred to as "the APD") or a linear sensor or the like is used. To image the light reflected from an eye to be examined, a synchronizing signal is input to the sensor. The imaging is performed in synchronization with the drive of the scanner.

For example, the OCT apparatus has two scanners, namely, a scanner that scans an eye to be examined in a horizontal direction and a scanner that scans the eye to be examined in a vertical direction. To obtain a single tomographic image with such a configuration, the scanner in the main scanning direction is driven for one line without driving the scanner in the sub scanning direction. Further, a three-dimensional image is obtained by driving the scanner in the sub scanning direction upon the completion of the main scan for one line thereby to shift in the sub scanning direction, thus repeating the main scan for a predetermined number of lines. At this time, in synchronization with the drive start timing of the main scan, the image acquisition is started, and upon the completion of the acquisition for a predetermined number of times of A-scans (the information in the depth direction at one point on an eye to be examined), the image acquisition is stopped.

However, in the actual scanner drive, there is a delay from the issuance of a drive instruction to a scanner until the actual drive position of the scanner reaches an instructed position. Therefore, if the drive start timing and the acquisition start timing are set to be the same, then an image is acquired at a position that is different from a desired position. This results in the occurrence of a positional displacement in the acquired image. A conceivable solution is to wait for a certain time after the drive instruction is issued to the scanner before starting the acquisition, so that an image can be acquired at a desired position. However, the time of the delay varies for each scanner or according to an environmental change or a change over time. For this reason, there has been a demand for measures to securely suppress the occurrence of the positional displacement.

Japanese Patent Application Laid-Open No. 2012-213490 describes an apparatus adapted to acquire an image by taking into account the operational difference between a scan in a forward direction and a scan in a backward direction in a reciprocal scan. However, in the apparatus, the time delay from the issuance of the drive instruction to the actual drive start is not taken into account.

The positional displacement of an image described above may badly affect an image diagnosis by a doctor and may cause the doctor to erroneously identify a lesion, resulting in a misdiagnosis.

SUMMARY OF THE INVENTION

In view of the above-described problem, an object of the present invention is to acquire an image at timing set by considering a time delay from the issuance of an instruction to a scanner until an actual drive position reaches an instructed position, thus acquiring an image with a least positional displacement.

To this end, an ophthalmologic apparatus according to the present invention includes:

a light scanning unit that scans measuring light on an eye to be examined;

an acquisition unit that receives light reflected from the eye to be examined and acquires a light receiving signal;

an instruction unit that instructs a drive position of the light scanning unit;

a position detection unit that detects a current position of the light scanning unit; and a measurement unit that measures a drive time delay from issuance of an instruction by the instruction unit until the current position reaches the instructed drive position, wherein the acquisition unit starts acquiring the light receiving signal at timing based on the drive time delay.

According to the present invention, an image is acquired at timing based on the time delay from the issuance of an instruction to a scanner until the actual drive position reaches an instructed position, thus making it possible to acquire an image with a least positional displacement.

Further features of the present invention will become apparent from the following description of exemplary embodiments with reference to the attached drawings.

DESCRIPTION OF THE EMBODIMENTS

Preferred embodiments of an ophthalmologic apparatus according to the present invention will now be described in detail in accordance with the accompanying drawings.

Figure 1:
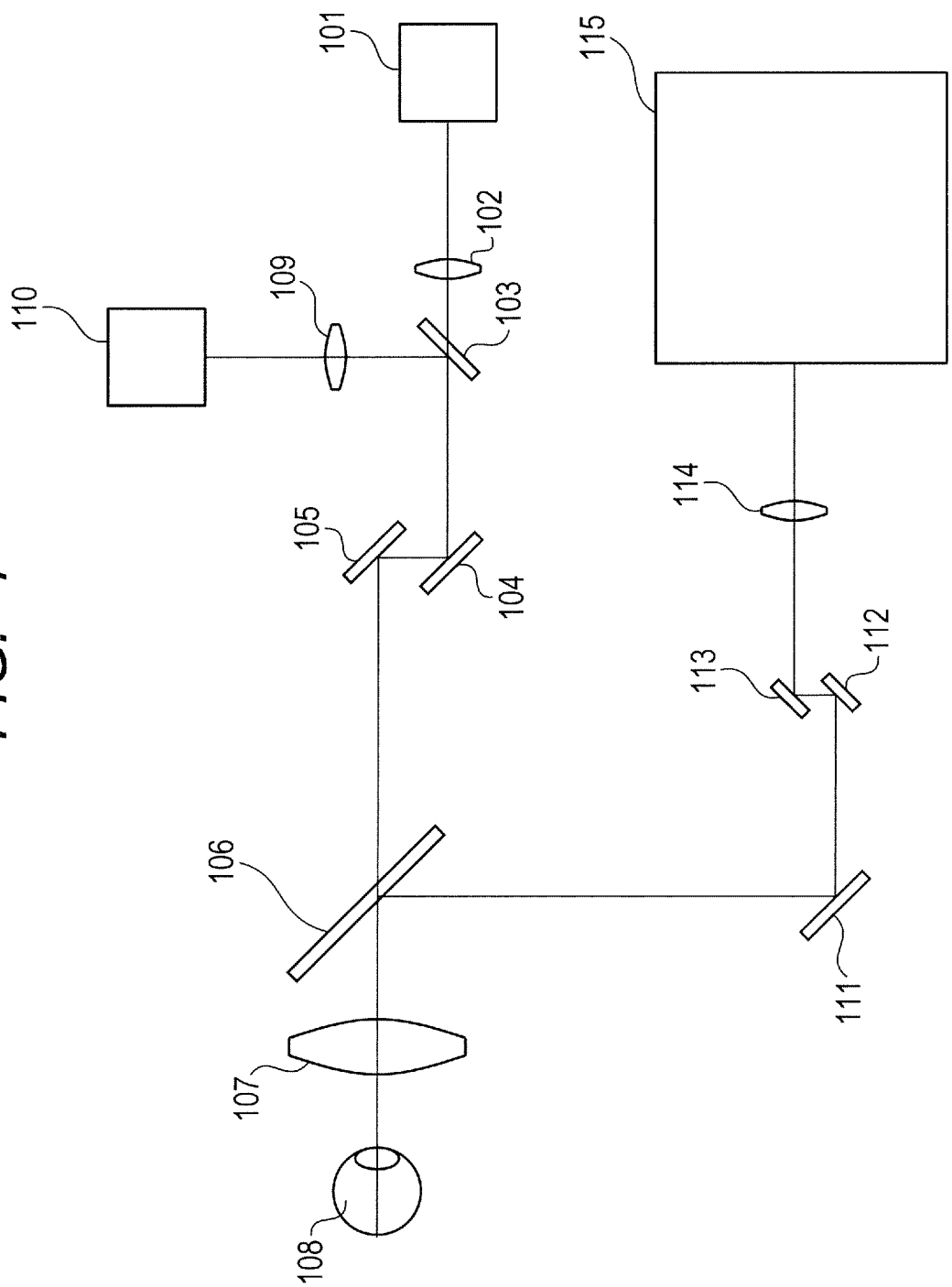
FIG. 1 is a diagram illustrating the configurations of the OCT apparatus and the SLO apparatus according to an embodiment of the present invention.

FIG. 1 illustrates an example of the ophthalmologic apparatus provided with the functions of the SLO and the OCT described below.

<SLO Unit>

First, an SLO unit will be described with reference to FIG. 1.

A laser light source 101 may use a semiconductor laser or a super luminescent diode (SLD) light source. Regarding the wavelength to be used, a near-infrared wavelength range of 700 nm to 1000 nm is used to reduce the glare to a subject when observing his/her fundus and to maintain the resolution. In the present embodiment, a semiconductor laser of a 780-nm wavelength is used.

The laser light emitted from the laser light source 101 turns into a parallel beam through a collimator lens 102, passes through a hole in a holed mirror 103 having a hole at the center thereof, and passes through an SLO-X scanner 104 and an SLO-Y scanner 105. The beam further passes through a beam splitter 106 and an eyepiece lens 107 before entering an eye to be examined 108.

In the following description, according to a coordinate system in the embodiments, the direction of an eye axis will be denoted by Z, and a horizontal direction relative to a fundus image will be denoted by X and a vertical direction relative thereto will be denoted by Y.

The beam incident upon the eye to be examined 108 is irradiated in the form of a spot beam to the fundus of the eye to be examined 108. The beam is reflected or scattered at the fundus of the eye to be examined 108 and then traces along the same light path back to the holed mirror 103. The reflected or scattered light is reflected off of the holed mirror 103 and received by an APD 110 through a lens 109, providing a signal that is proportional to the reflection/scattering intensity of a spot of the fundus.

Further, a two-dimensional image of the fundus can be obtained according to the acquired reflection/scattering intensity by raster scanning the SLO-X scanner 104 and the SLO-Y scanner 105.

<OCT Unit>

Figure 2:
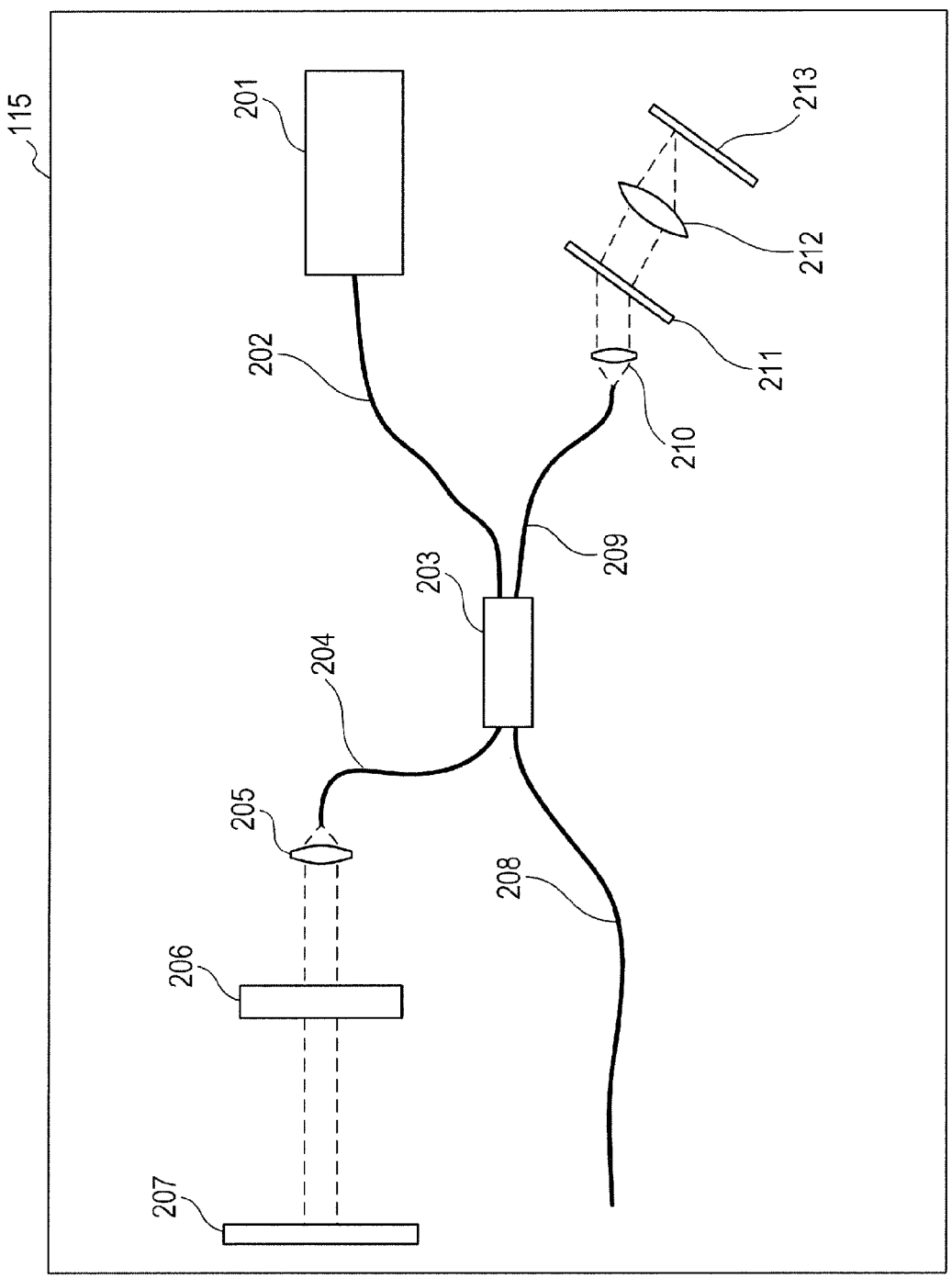
FIG. 2 is a diagram illustrating the configuration of an OCT optical system unit in the embodiment illustrated in FIG. 1.

Referring now to FIG. 1 and FIG. 2, an OCT unit in the present embodiment will be described.

An OCT optical system 115 splits low-coherence light into reference light and signal light, combines the signal light passing through the eye to be examined 108 and the reference light passing through a reference object so as to generate interfering light, and outputs a signal obtained by dispersing the interfering light.

A low-coherence light source 201 is constituted of a broadband light source that outputs low-coherence light. The broadband light source in the present embodiment uses a super luminescent diode (SLD) light source, which exhibits low coherence. The low-coherence light includes light having a near-infrared range wavelength and has a coherence length of approximately several tens of micrometers. The wavelength of the low-coherence light ranges, for example, from approximately 800 nm to approximately 900 nm.

The low-coherence light output from the low-coherence light source 201 is led into a photo coupler 203 through an optical fiber 202. The optical fiber 202 is usually formed of a single-mode fiber. The photo coupler 203 splits the low-coherence light into reference light and signal light.

The reference light generated by the photo coupler 203 is led by an optical fiber 204 to be formed into a parallel luminous flux through a collimator lens 205, and passed through a glass block 206, which serves as a dispersion compensating means for matching the dispersion characteristics of the reference light and observation light, and reflected off of a reference mirror 207. The reflected reference light traces the same optical path to enter the optical fiber 204.

The reference mirror 207 is movable in the direction in which the reference light advances. This makes it possible to adjust the distance between the reference light and the observation light by the eye axis length of the eye to be examined 108 or the distance between the eyepiece lens 107 and the eye to be examined 108.

Meanwhile, the measuring light generated by the photo coupler 203 is sent through a fiber 208 to a scanner and an eyepiece section of the OCT unit in FIG. 1, which will be discussed later.

The measuring light from the OCT optical system 115 turns into a parallel beam through a collimator lens 114 and then passes through an OCT-X scanner 113 and an OCT-Y scanner 112. The beam is then reflected off of a mirror 111 and a beam splitter 106, passes through the eyepiece lens 107 and enters the eye to be examined 108. As with the SLO, the beam that has entered the eye to be examined 108 is reflected and scattered at the fundus and traces the same light path back to the OCT optical system 115.

The returned light reflected from the eye to be examined is input again to the fiber 208, and the reflected light that has been led to the photo coupler 203 interferes with the reference light and forms multiplex light. The multiplexed light is passed through an optical fiber 209, formed into parallel light through a collimator lens 210, and thereafter dispersed through a diffraction grating 211, finally being formed into an image on a linear sensor 213 through a lens 212. The linear sensor 213 may use a CCD sensor, a CMOS sensor, or the like. Thus, a signal resulting from the dispersion of the interfering light can be obtained from the linear sensor 213. The configuration exemplified by the linear sensor 213 or the foregoing APD 110 constitutes an acquisition unit for receiving the light reflected from an eye to be examined and acquiring a light receiving signal in the present invention.

Further, a tomographic image or a three-dimensional image of a fundus can be obtained by raster scanning the OCT-X scanner 113 and the OCT-Y scanner 112.

Here, each of the SLO-X scanner 104, the SLO-Y scanner 105, the OCT-X scanner 113, and the OCT-Y scanner 112 is constituted of a mirror fixed to a rotating shaft, an actuator that rotatively drives the rotating shaft, and a rotary encoder that detects a rotational position. Further, the configuration exemplified by these scanners constitutes an optical scanning unit that scans measuring light on an eye to be examined in the present invention.

<Control Unit>

Figure 3:
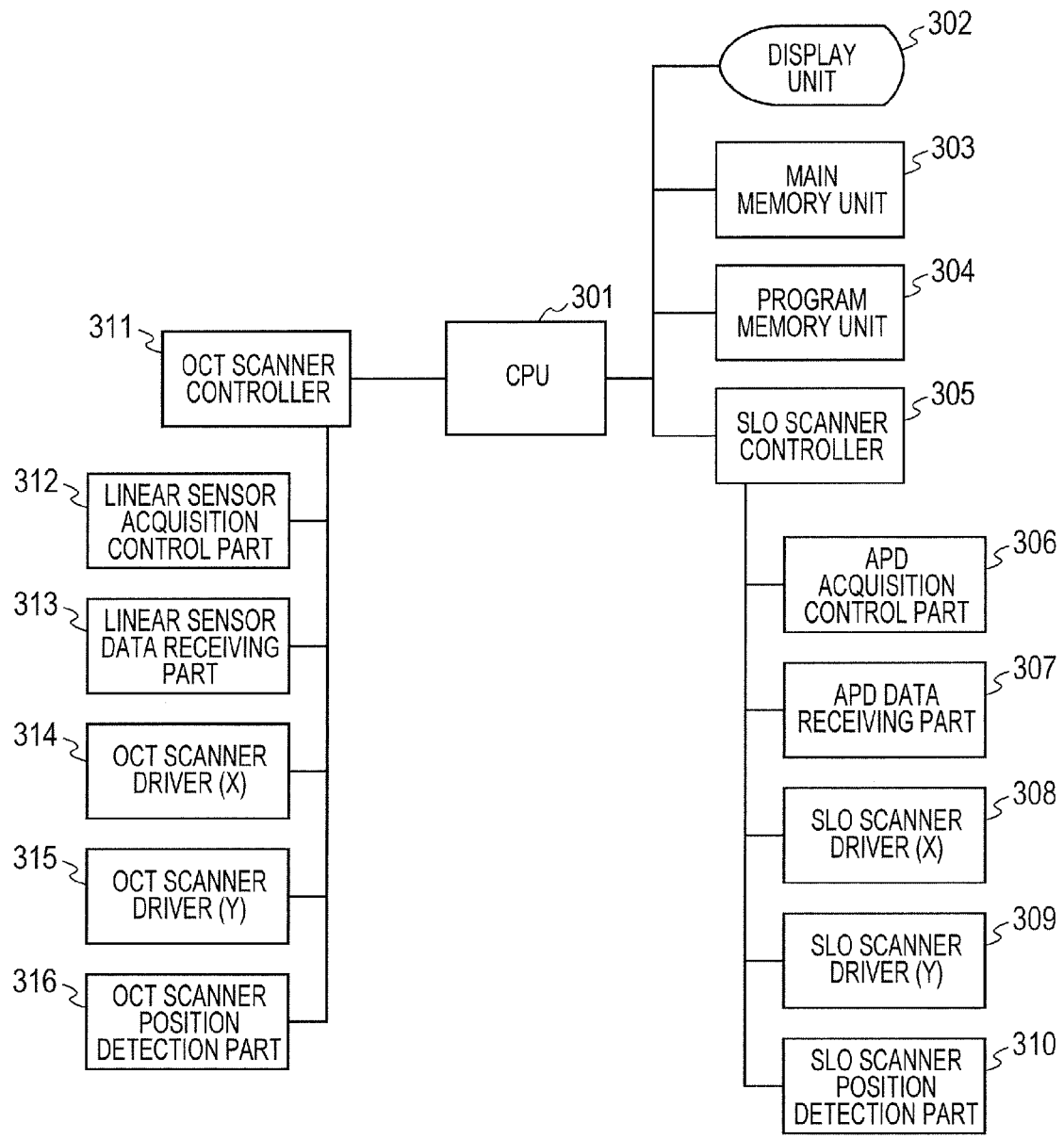
FIG. 3 is a block diagram illustrating the configuration of a control system in the embodiment illustrated in FIG. 1.

Referring now to FIG. 3, a control unit will be described.

A central processing unit (CPU) 301 is connected to a display unit 302, main memory unit 303 (RAM), a program memory unit 304 (ROM), an SLO scanner controller 305, and an OCT scanner controller 311.

The SLO scanner controller 305 controls the drive of the SLO scanner by an SLO scanner driver (X) 308 and an SLO scanner driver (Y) 309 according to an instruction from the CPU 301. An SLO scanner position detection part 310 enables the CPU 301 to know the scanning position of SLO measuring light. The SLO scanner position detection part 310 is capable of detecting the position of the SLO scanner (the scanning position of the SLO measurement light) on the basis of an output of the foregoing rotary encoder. Further connected are an APD acquisition control part 306 and an APP data receiving part 307 that receives APP data.

In response to an instruction from the CPU, the OCT scanner controller 311 controls the drive of the OCT scanners by an OCT scanner driver (X) 315 and an OCT scanner driver (Y) 314. An OCT scanner position detection part 316 enables the CPU to recognize the scanning position of OCT measuring light. More specifically, the OCT scanner position detection part 316 is capable of detecting the position of the OCT scanner, i.e. the scanning position of the OCT measuring light, on the basis of an output of the foregoing rotary encoder. Further connected are a linear sensor acquisition control part 312 that controls the acquisition timing of the linear sensor, which is an output of the OCT, and a linear sensor data receiving part 313, which receives linear sensor data.

In the configuration described above, the APD signal of the SLO and the dispersed linear sensor signal of the OCT are supplied to the CPU 301. The CPU 301 analyzes the detection signals to form a tomographic image of the fundus or a fundus image. Further, the CPU 301 executes the following control processing flow to control the apparatus according to a program stored in the program memory unit 304.

<SLO Processing>

The following will describe the acquisition processing carried out by the SLO.

Defaults for the Y-scan center position, the scan speed, the scan width in a Y-direction, and the number of imaging pixels are set at the SLO scanner controller 305. Thus, the beam of the SLO scans a retina. At this time, the APD outputs a signal proportional to the reflection/scattering intensity of the retina, and the signal is supplied to the CPU 301 through the intermediary of the APD data receiving part 307.

The CPU 301 is capable of acquiring a retina image by placing the intensity of the APD signal at the scanner position received from the SLO scanner controller and also capable of displaying the retina image on the display unit 302.

<OCT Processing>

The following will describe the acquisition processing carried out by the OCT.

The CPU 301 sets X and Y-scan center positions, a scan speed, the scan widths in the X and Y-directions, the main scanning direction, and the number of times of A-scans at the OCT scanner controller 311. Thus, the signal light from the OCT unit scans on the retina. At this time, an output of the linear sensor 213 of the OCT optical system 115 is supplied to the CPU 301 through the intermediary of the linear sensor data receiving part 313.

The CPU 301 processes frequencies, wavenumber transform FFT or the like on the main memory unit 303 according to a program in the program memory unit 304 thereby to obtain the information in the depth direction of the retina. Based on the information and the positional information from the OCT scanner controller 311, the tomographic image or the three-dimensional image of the retina can be obtained, and the obtained image can be displayed on the display unit 302. Further, a two-dimensional fundus image similar to the image acquired by the SLO can be acquired by using the luminance value of a tomographic image at each position on a fundus surface, which is obtained at the time of a raster scan. Hence, embodiments involving the OCT acquiring apparatus will be described hereinafter.

<Scanner Driving Method and Image Acquiring Method>

The following will describe a scanner driving method and an image acquiring method.

Figure 4A:
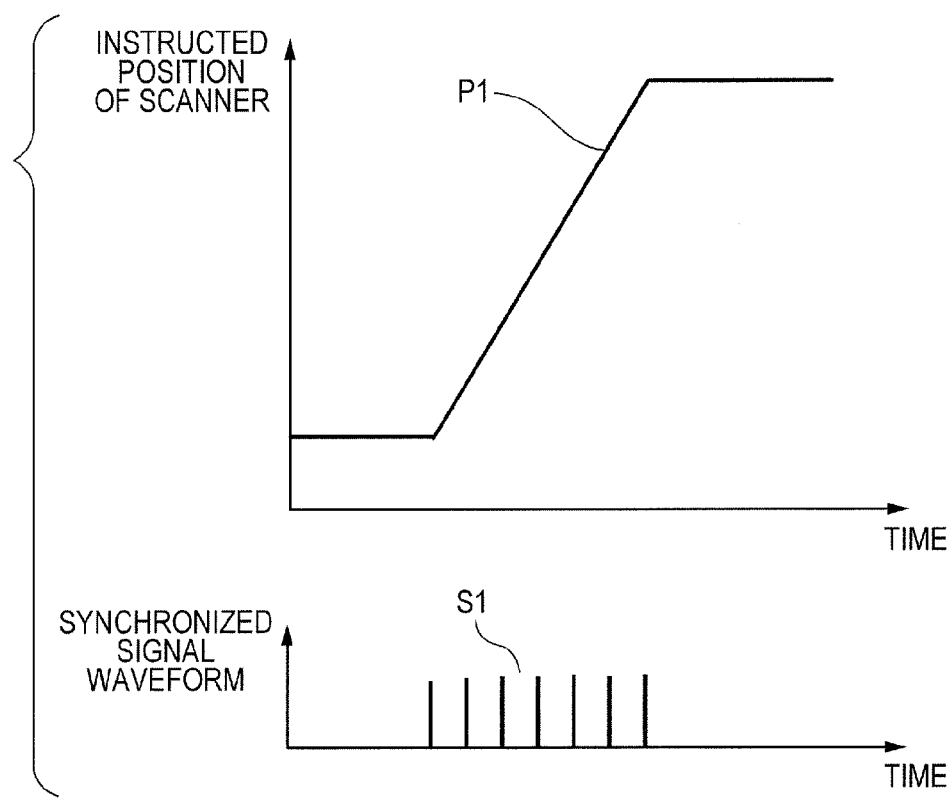
FIG. 4A is a diagram illustrating the relationship between a drive instruction of a scanner and a corresponding positional waveform.

FIG. 4A illustrates an instructed drive position waveform P1, which is a positional waveform corresponding to a drive instruction of a scanner, and a synchronizing signal waveform S1, the signal being a trigger signal. The OCT scanner driver X 314 and the OCT scanner driver Y 315 instruct drive positions to the OCT-X scanner 113 and the OCT-Y scanner 112. In synchronization with the timing, the linear sensor acquisition control part 312 starts transmitting the synchronizing signal to the linear sensor 213 thereby to start the acquisition. Upon completion of the acquisition for a predetermined number of A-scans (the information in the depth direction at one spot on an eye to be examined), the acquisition is stopped. More specifically, the linear sensor acquisition control part 312 transmits the synchronizing signal to the linear sensor 213 thereby to read an output of the linear sensor 213. From a different viewpoint, the linear sensor 213 outputs a value based on the quantity of received light based on the synchronizing signal. The APD acquisition control part 306 is also capable of reading an output of the APD 110 on the basis of the synchronizing signal.

Figure 4B:
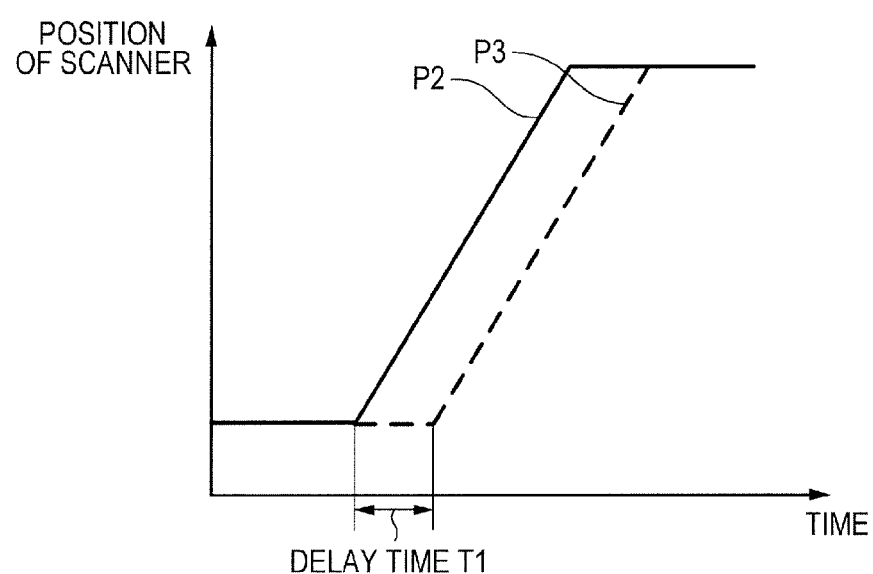
FIG. 4B illustrates the relationship between an instructed positional waveform and a current position.

FIG. 4B illustrates the relationship between the instructed drive position waveform of a scanner described above and a current position waveform indicative of a current scanner position. The solid line indicates an instructed drive position waveform P2, while the dashed line indicates a current position waveform P3. The current position waveform can be acquired by a rotary encoder or the like provided in the scanner. The configuration exemplified by the rotary encoder corresponds to that of a position detection unit that detects the current position of the scanner, which is a light scanning unit. There is a delay from the moment a scanner driver instructs a drive position to the scanner until the moment the current position of the scanner reaches the instructed position. The time delay T1 ranges from approximately 100 µs to approximately 300 µs depending on the performance of an actuator, the control method or tuning. The authors have confirmed that the time delay T1 remains substantially constant within the operation guaranteed speed range of the scanner even if the drive speed changes.

Figure 5A:
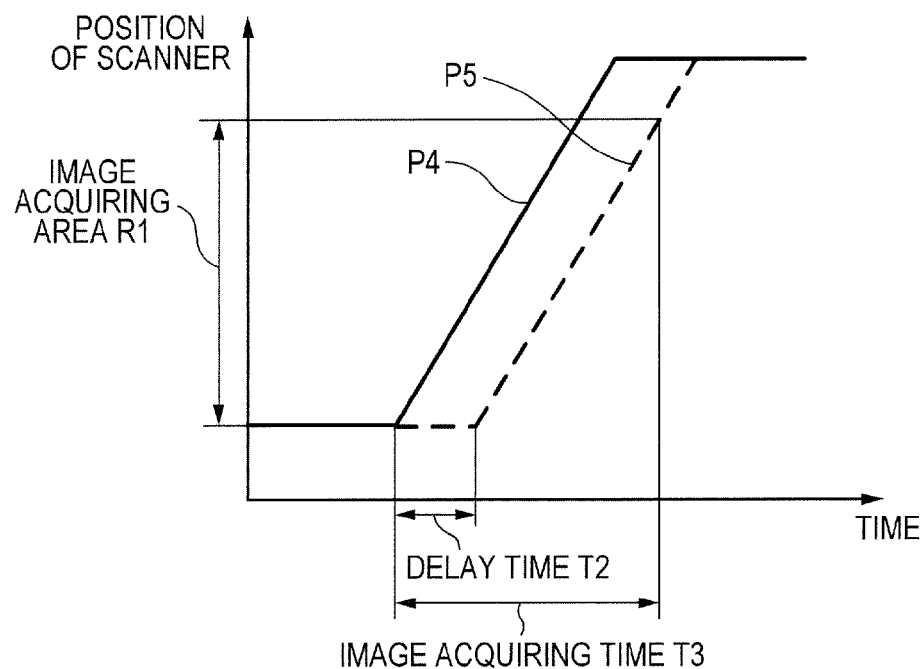
FIG. 5A is a diagram illustrating the relationship between a drive instruction of a conventional scanner and corresponding image acquiring time.
Figure 5B:
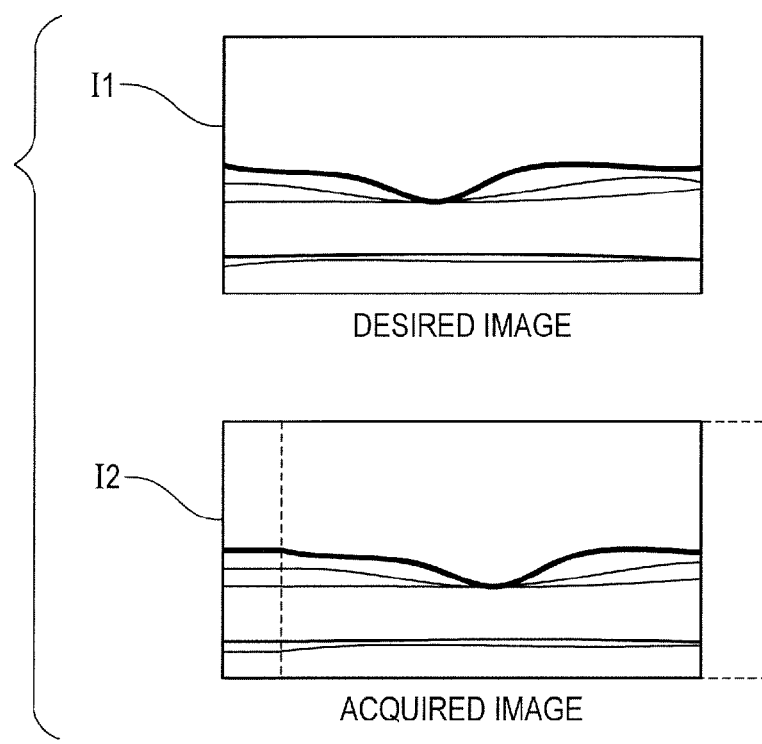
FIG. 5B is a diagram illustrating a tomographic image acquired.

Therefore, if the drive instruction start timing at which the scanner driver issues an instruction on a drive position to the scanner and the acquisition start timing at which the linear sensor 213 starts acquisition are set to be the same, then a fundus image is acquired at a position that deviates from a desired position (FIG. 5A). As a result, when, for example, an attempt is made to acquire a tomographic image I1 in FIG. 5B, a tomographic image I2 exhibiting a positional displacement from the tomographic image I1 is inconveniently acquired.

Although the drive speed remains constant, drive position waveform P5 in FIG. 5A actually has an acceleration region until the constant speed is reached and a deceleration region until coming to a halt. If images are acquired throughout the period from a drive start to a drive stop, then the amount of scanner drive per 1A-scan in the acceleration region and the deceleration region differs relative to the drive amount in a constant speed region, so that both ends of an acquired image may be distorted. In order to suppress the distortion, images could be acquired only in the constant speed region, excluding the acceleration region and the deceleration region. If, however, the acceleration region and the deceleration region are long, then it would be necessary to drive the scanner for a longer distance accordingly, resulting in a lower imaging frame rate. For example, in the case of 128A-scans at a 70 kHz image sampling rate for a 12-mm length, the scanning time through the acceleration region and the deceleration region takes approximately 400 µs. Further, if the scan is carried out the 128A-scans for 96 times over an area measuring 12 mm×10 mm, then the frame rate drops from 2.4 fps to 1.7 fps. Thus, the quality of an image to be acquired and the frame rate have a trade-off relationship, so that the method to be used has to be selected according to the conditions of images desired to be acquired.

To simplify a description, an example of the case where images are acquired throughout the period from a drive start to a drive end will, be described below.

According to the prior art, in order to cope with the problem of the tomographic image I2 exhibiting the positional displacement, the acquisition is started after waiting for a 2-minute time delay T following the issuance of an instruction on a drive position. A fixed value has been determined for the waiting time on the basis of a study result in product development.

However, the tuning of an actuator varies from one actuator to another. In addition, the operating characteristics of the actuator change due to a change in the temperature of the apparatus after a startup or an environmental change or a time dependent change after the apparatus is shipped out. Accordingly, time delay T2 changes for each apparatus due to an environmental change or a time-dependent change. Because of the change in the time delay T2, setting the waiting time to a fixed value inconveniently leads to the positional displacement of an acquired image.

Figure 6A:
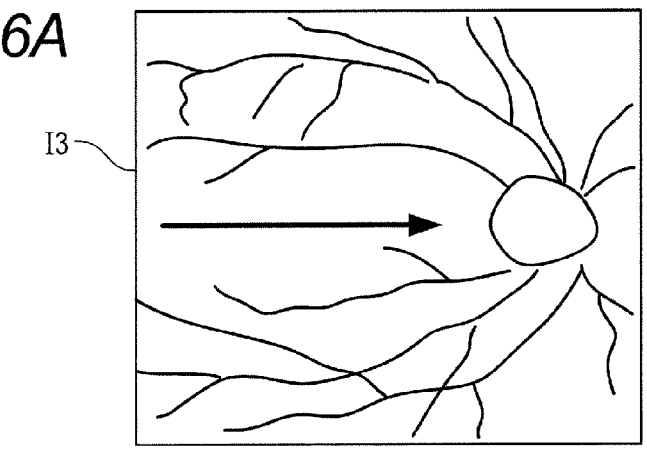
FIG. 6A is a diagram illustrating the scanning positions of measuring light.
Figure 6B:
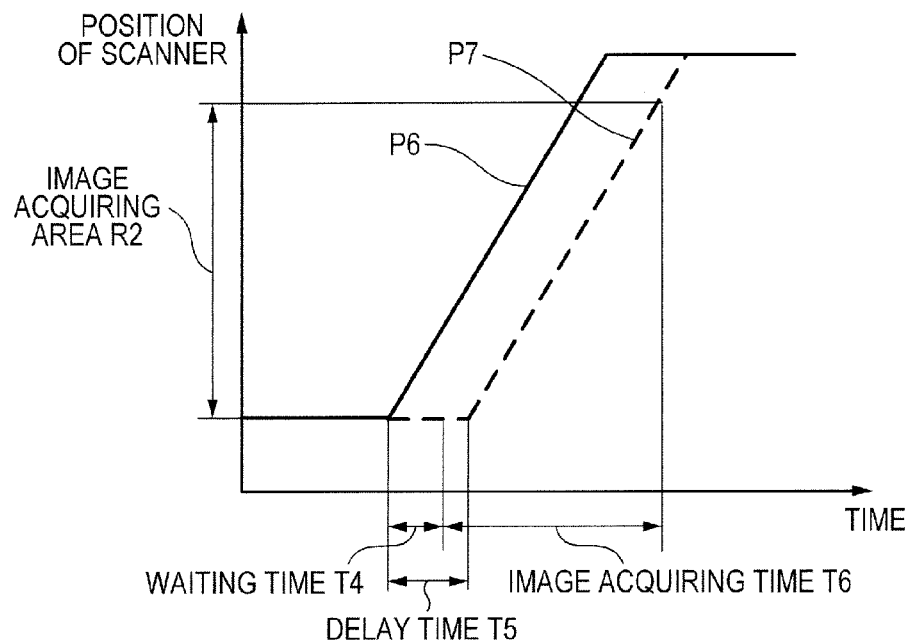
FIG. 6B is a diagram illustrating the operation of the scanner during a tomographic image scan, and FIG. 6C a diagram illustrating an image obtained by the operation.
Figure 6C:
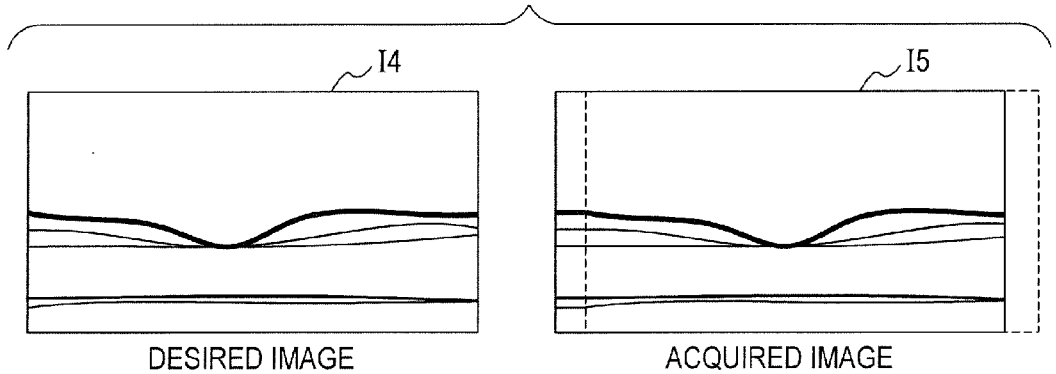

A description will be given of a case where, for example, the scanner in the main scanning direction is driven to scan the measuring light on the fundus without driving the scanner in the sub scanning direction (FIG. 6). An arrow I3 in the solid line in the drawing indicates the scanning trajectory. FIG. 6B illustrates an instructed drive position waveform P6 and a current position waveform P7 at that time. If a time delay T5 is longer than waiting time T4, then the acquisition is started before the drive of the scanner is started and the acquisition is stopped before the drive is stopped (the acquisition time remains within the range of T6). FIG. 6C illustrates the resulting tomographic image. As illustrated in FIG. 6C, a tomographic image I5 of an acquisition range R2, which deviates from the tomographic image I4 of a desired acquisition range of the fundus, is undesirably acquired. In this example, the left end of the displayed image is acquired with the drive stopped, thus showing an image having the pixels of the same value arranged in the horizontal direction, while the right end of the image showing an image cut off in the middle because the acquisition is stopped in the middle of the range desired to be acquired.

Figure 7A:
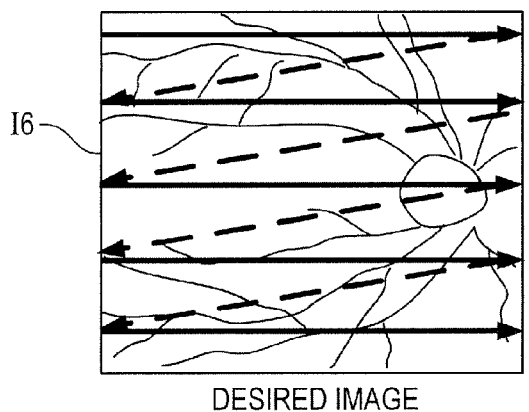
FIG. 7A is a diagram illustrating a forward scan of the measuring light.
Figure 7B:
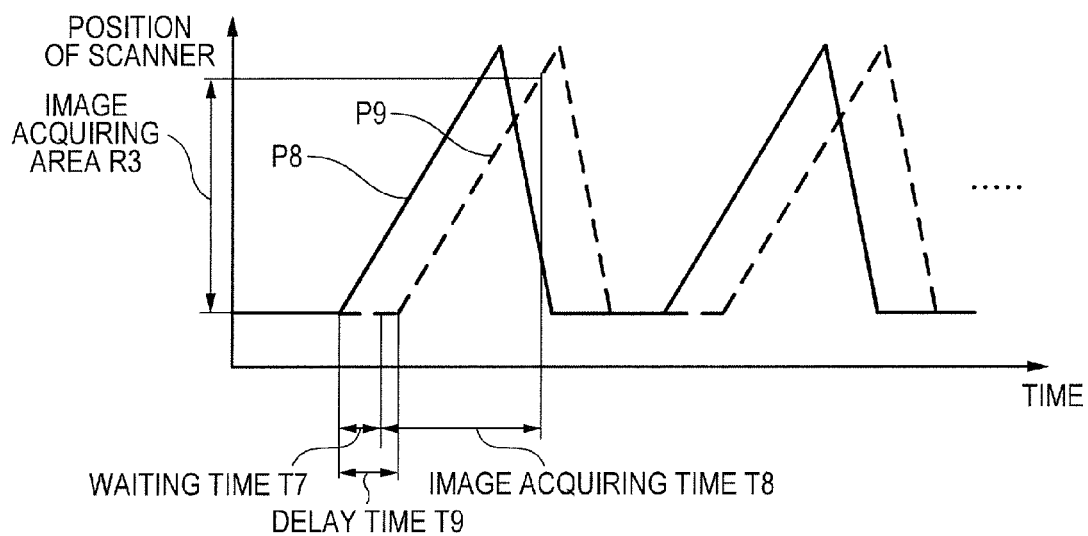
FIG. 7B is a diagram illustrating the operation of the scanner.
Figure 7C:
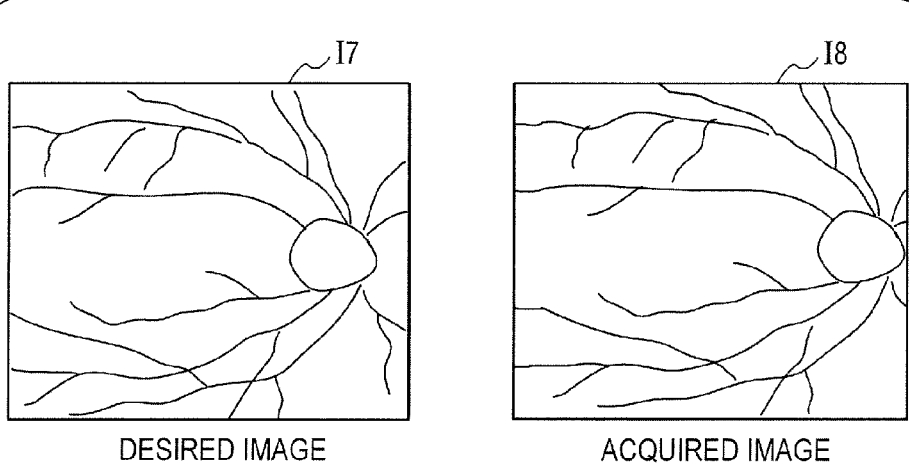
FIG. 7C is a diagram illustrating an image obtained by the operation.

Further, as described above, a fundus image is acquired by repeating main scan in the forward direction while shifting the scanner in the sub scanning direction (refer to the raster scan illustrated in FIG. 7A). An arrow I6 indicated by the solid line in the drawing denotes the scanning trajectory during the acquisition. The then luminance values of the tomographic image at each position on the fundus surface can be used to obtain a two-dimensional fundus image. FIG. 7B illustrates a then instructed drive position waveform P8 and a current position waveform P9. If a time delay T9 is longer than waiting time T7, then the acquisition is started before the drive of the scanner is started, and stopped before the drive is stopped (the acquisition time remains within the range of T8). FIG. 7C illustrates a resulting fundus image obtained to acquire the luminance values. As illustrated in FIG. 7C, a tomographic image I8 of an acquisition range R3, which deviates from the image of a desired acquisition range I7 of the fundus, is undesirably acquired. Hence, as with the tomographic image, the fundus image has the left end thereof formed of the pixels of the same value arranged in the horizontal direction and the right end thereof formed of an image cut off in the middle. For example, in the case of a 70-kHz acquisition sampling rate, if the time delay is 60 µs longer than the waiting time, then the positional displacement of approximately 4 pixels will appear on an acquired image. This means that, if the 128A-scan is carried out for a length of 12 mm, then the acquisition position will be displaced by 400 µm on the fundus surface.

When the main scan is repeated in the forward direction as illustrated in FIG. 7A, the scanner in the main scanning direction is returned to the drive start Position upon the completion of the main scan for one line before starting the next main scan. At this time, the scanner must be driven for a longer distance than the main scan distance, inconveniently taking extra time. This results in a lower acquisition frame rate.

Figure 8A:
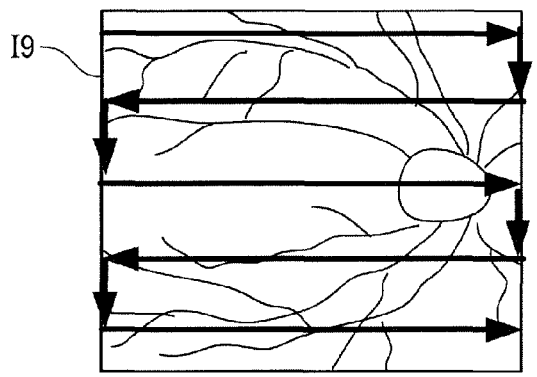
FIG. 8A is a diagram illustrating a reciprocal scan of the measuring light.
Figure 8B:
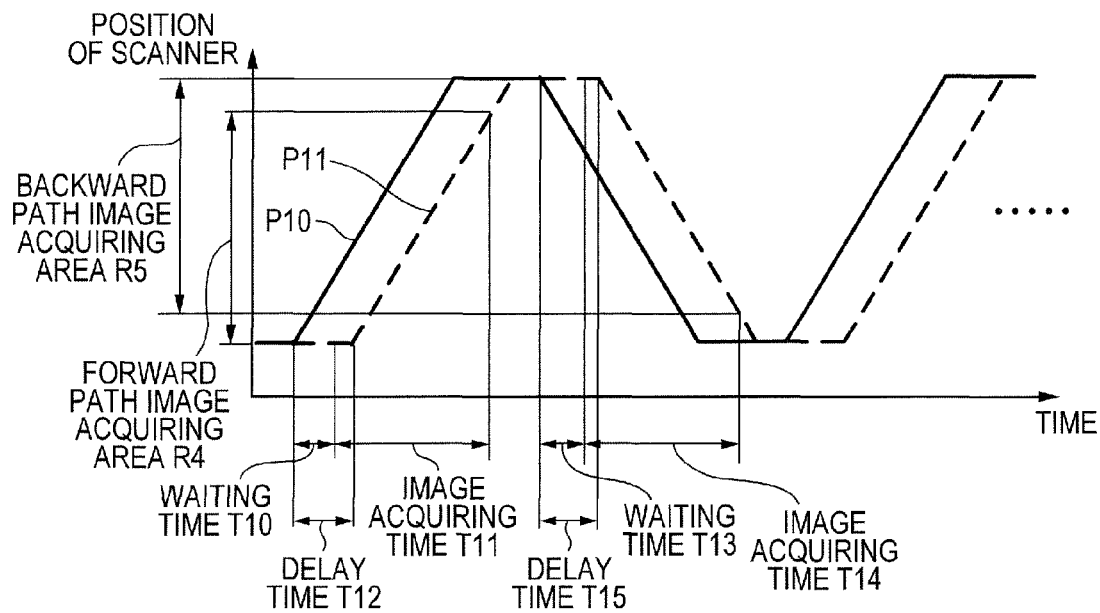
FIG. 8B is a diagram illustrating the operation of the scanner.
Figure 8C:
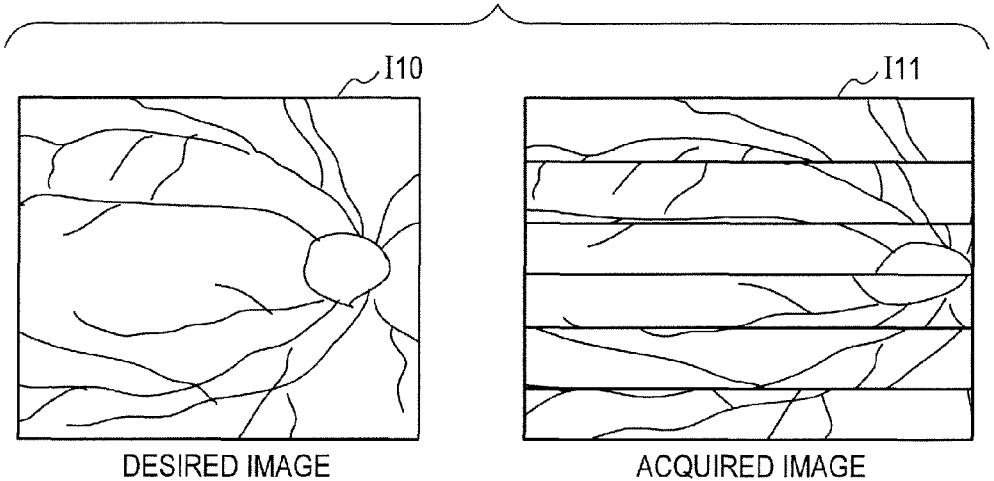
FIG. 8C is a diagram illustrating an image obtained by the operation.

In order to increase the acquisition frame rate, therefore, a reciprocal scan may be carried out, in which the scanner is driven only in the sub scanning direction after the main scan in the forward direction is completed and then the main scan is carried out in the return direction. This is continuously and alternately repeated in the reciprocal scan. How this scan is carried out on the fundus is illustrated by solid arrows I9 in FIG. 8A. Further, FIG. 8B illustrates an instructed drive position waveform P10 at that time and a current position waveform P11. If a time delay T12 is longer than waiting time T10 in a forward scan, then an image of acquisition range R4 is acquired during acquisition time T11. Further, if a time delay T15 is longer than waiting time T13 in a return scan, then an image of acquisition range R5 is acquired during acquisition time T14. As a result, as illustrated in FIG. 8C, an image I11 is inconveniently acquired, in which the range in which the in is acquired by the forward scan disagrees with the range in which the image is acquired by the return scan, in contrast to a fundus image I10 desired no be acquired. In this example, the line image acquired by the forward scan shows the left end thereof formed of an image of the pixels of the same value arranged in the horizontal direction and the right end thereof formed of an image cut off in the middle, and the line image acquired by the return scan has the left end thereof formed of an image cut off in the middle and the right end thereof formed of an image of the pixels of the same value arranged in the horizontal direction. Thus, the acquired fundus image exhibits a positional displacement that is more marked than the image acquired only by the forward scan.

The positional displacement of the image may not only prevent a doctor from making a diagnosis based on an image but also cause the doctor to erroneously identify a lesion with a consequent misdiagnosis.

First Embodiment

According to the present embodiment, before acquiring an image of an eye to be examined, the time required from the moment a drive position is instructed to a scanner until the moment the current position of the scanner reaches the instructed position is measured as an acquisition time delay or a time delay. Further, at the time of imaging the eye to be examined, the acquisition of an image, i.e. a light receiving signal, is started by taking the time delay into account or at a timing based on the time delay.

First, the following two methods of measuring the time delay will be described.
(I) Method in which the time delay is measured each time a predetermined position is reached; and
(II) Method in which the time delay is measured for each predetermined interval.

First, the method (I) will be described with reference to FIG. 9A. A CPU 301 instructs an OCT scanner controller 311 to set a measurement scanning direction and a measurement position and to carry out the scan for measuring the time delay. In this case, it is assumed that, for example, the forward direction is selected as the measurement scanning direction and MP1 is set as the measurement position. The OCT scanner controller 311 starts transmitting an instruction to an OCT scanner driver X 314 and an OCT scanner driver Y 315 such that the scanner reaches the instructed position of, for example, the scan pattern of a velocity V1 illustrated in FIG. 9A. The instructed position is the position instructed by the driver at the time of driving the scanner, and refers to the drive position based on the instruction at which the scanner is positioned. At the same time, the OCT scanner position detection part 316 continues to sequentially transmit the current position, which is being continuously received from the scanner, to the OCT scanner controller 311. Further, the OCT scanner controller 311 detects that the current position has reached the measurement position MP1 and transmits the then instructed position denoted by MP2 to the CPU 301. In other words, the CPU 301 acquires the instructed position MP2 and the current position. The MP1 denotes, for example, substantially the center of the range of the scan in the main scanning direction. Setting the MP1 as described above makes it possible to determine the time delay while avoiding an acceleration region and a deceleration region as much as possible. The MP1 may be set at any position rather than being limited to substantially the center of the range of the scan in the main scanning direction. In the present embodiment, the time delay is measured only at one position, namely, MP1; however, the time delay in the present invention is not limited thereto. Alternatively, the time delay may be measured at a plurality of locations and a mean value may be obtained.

Then, the CPU 301 uses the instructed position MP2 and the current position to calculate a scanner drive time delay T16 according to the following expression.

$$T16 = (MP2 - MP1)/V1 \quad (1)$$

The calculation result is stored in a main memory unit 303 as the scan time delay.

Figure 9A:
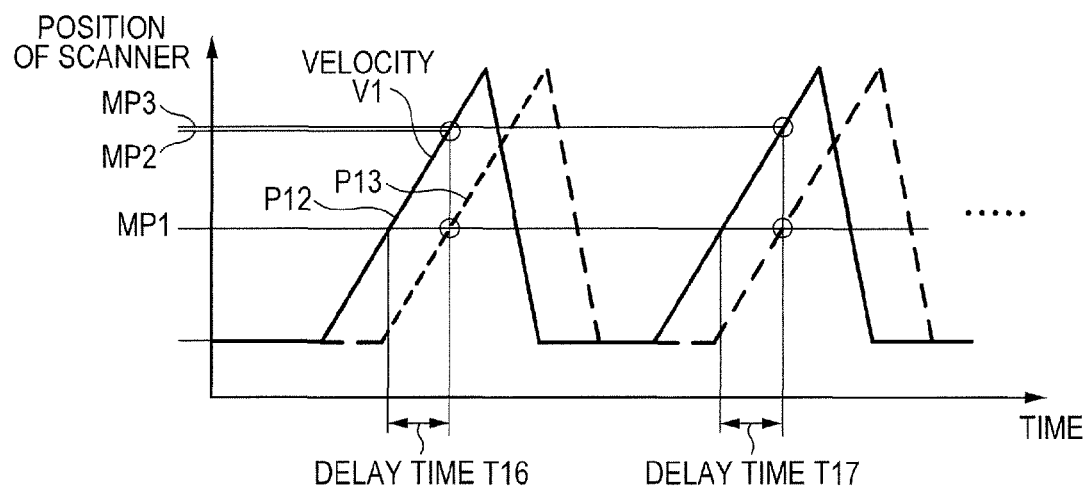
FIGS. 9A and 9B are diagrams illustrating a method of measuring the drive time delay of the scanner in a first embodiment.

As illustrated in FIG. 9A, the scan is repeated for a predetermined number of times, and the time delay for each scan is recorded in the main memory unit 303. Upon completion of the measurement, the mean value of the time delays is calculated and the obtained mean value is stored in the main memory unit 303 as the time delay used for imaging the eye to be examined. The example illustrates the case where the current position is monitored and the instructed position MP2 at the moment the current position reaches the measurement position MP1 is transmitted to the CPU 301. Alternatively, however, the instructed position may be monitored and the current position at the moment the instructed position reaches the measurement position may be transmitted to the CPU 301.

The method (II) will now be described with reference to FIG. 9B. The CPU 301 sets a measurement time interval ΔT1 at the OCT scanner controller 311.

Next, as with the method (I), the CPU 301 carries out the scan for measurement and acquires a current position. Then, the OCT scanner controller 311 transmits the instructed position and the current position to the CPU 301 at every time interval ΔT1. Then, as with the method (I), the time delay is calculated according to expression (I). At this time, the measurement data acquired in regions in which the scanner is not driven at a constant speed, which regions are denoted by the cross marks (x) in FIG. 9B, is not valid data, so that the data is discarded and not used. The scan is repeated until valid measurement data is acquired for a predetermined number of times.

According to the method (I), only valid data is measured, so that the scan time for measurement remains constant. Further, it is necessary to monitor in real time whether a current position has reached a measurement position. Meanwhile, according to the method (II), the scan is repeated until valid data is acquired for a predetermined number of times, so that the scan time for measurement may be prolonged. However, it is not required to monitor in real time whether a current position has reached a measurement position.

The current position acquired from the scanner is updated every tens of micro-second, thus making it difficult timewise to monitor the current time and to perform processing in real time by software of a microcomputer or the like. Therefore, the method (I) should be used when operating the OCT scanner controller 311 by hardware, such as circuitry, and the method (II) should be used when operating the OCT scanner controller 311 by software of a microcomputer or the like.

Figure 9B:
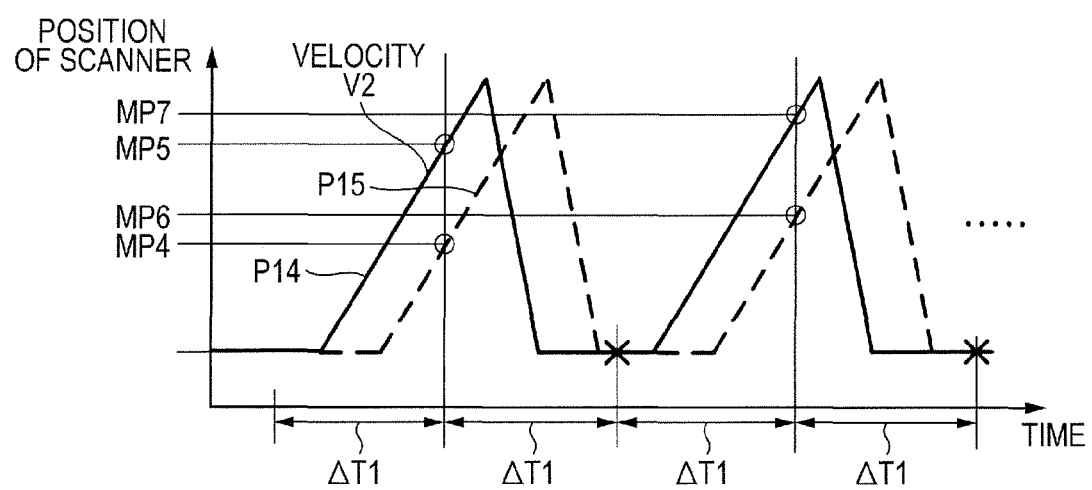

FIG. 9A and FIG. 9B illustrate an example of the measurement only in the forward direction. Alternatively, however, the reciprocal scan may be carried out to measure the time delay in the forward scan and the time delay in, the return scan, and the mean value thereof may be calculated.

Further, the value of the current position is acquired from a signal retained at an encoder of the scanner, the signal being received by the OCT scanner position detection part 316 and then processed by the OCT scanner controller 311. Strictly speaking, therefore, the value of the current position acquired by the OCT scanner controller 311 indicates the position of the scanner before encoder acquisition time TE rather than the current position. The encoder acquisition time TE is approximately 60 μs. Hence, in order to accurately determine a time delay TD from the issuance of an instructed position until the scanner actually reaches the instructed position, the following expression must be used to subtract the encoder acquisition time TE from the time delay, which has been calculated according to expression (1). The encoder acquisition time TE is, for example, a value dependent upon the specifications of the encoder, and the ophthalmologic apparatus retains the encoder acquisition time TE as a preset value.

$$TD=T16-TE \quad (2)$$

Figure 10:
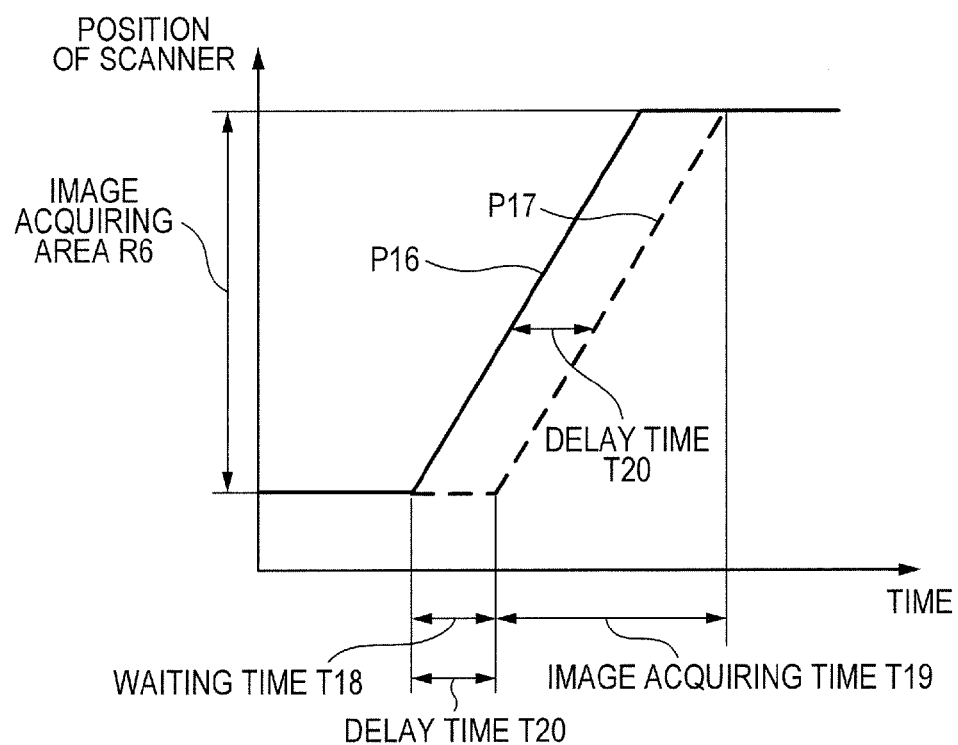
FIG. 10 is a diagram illustrating the relationship between the sensor acquisition timing and the then time delay in the first embodiment.

Referring to FIG. 10, a description will be given of the method of starting image acquisition at acquisition timing which takes the time delay into account or which is based on the time delay at the time of imaging an eye to be examined. The solid line in the chart of FIG. 10 denotes an instructed drive position waveform P16, and the dashed line denotes a current position waveform P17. From the timing at which a drive start is instructed to the OCT scanner driver X 314 and the OCT scanner driver Y 315, the OCT scanner controller 311 waits for the same time T18 as a time delay T20 and then instructs a linear sensor acquisition control part 312 to start acquisition. Using the method described above makes it possible to reduce the positional displacement of an acquired image.

Although the description has been given of the example in which the time delays only on one axis are measured, the OCT-X scanner 113 and the OCT-Y scanner 112 are independent actuators and therefore different in characteristics. For this reason, the time delay of each of the scanners of the two axes, namely, X and Y, should be measured. At this time, time delays on the two axes can be simultaneously measured to shorten the measurement time.

When measuring the time delays on the two axes, X and Y, of the scanners, which one of the time delays is to be used for the acquisition will be described below. In the OCT scan, the scan is frequently carried out by setting either the X-direction or the Y-direction as the main scanning direction relative to a fundus surface. Therefore, when a scan pattern to be implemented is determined, the CPU 301 determines which of the X-direction or the Y-direction is to be adopted as the main scanning direction. The time delay of the scanner carrying out the main scan should be set as the time delay to be used for imaging an eye to be examined. The time delay of the scanner carrying out the main scan should be used, because images are acquired by scanning light in the main scanning direction.

Further, the measurement of the drive time delay of the scanner is started at at least one of the timings when the ophthalmologic apparatus is started, up, a patient having an eye to be examined changes, the eye to be examined is switched from the right eye to the left or vice versa, and the acquisition of a light receiving signal is started, i.e. the start of the acquisition.

Second Embodiment

Figure 11:
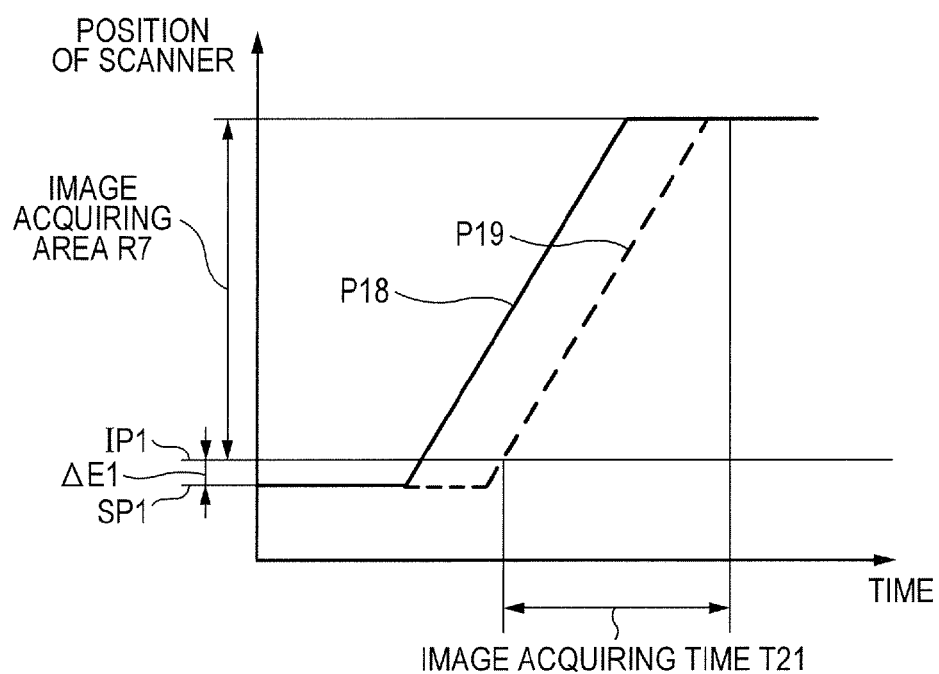
FIG. 11 is a diagram illustrating the relationship between the sensor acquisition timing and the then time delay in a second embodiment.

In the first embodiment, the time delay is measured before imaging an eye to be examined. Alternatively, however, for each scan at the time of imaging an eye to be examined, the image acquisition start position may be detected and the acquisition may be started. Referring to FIG. 11, the present embodiment will be described. A CPU 301 sets an acquisition start position IP1 at an OCT scanner controller 311. At the time of the acquisition, the CPU 301 instructs the OCT scanner controller 311 to carry out a scan and starts transmitting a drive instruction for implementing, for example, the scan pattern illustrated in FIG. 11. At the same time, an OCT scanner position detection part 316 continues to transmit a current position to the OCT scanner controller 311. Then, the OCT scanner controller 311 detects that the current position has reached the acquisition start position IP1 and issues an acquisition instruction to a linear sensor acquisition control part 312 and starts the acquisition. In other words, the CPU 301 in the present embodiment has a module region that functions as an acquisition start position detecting unit which detects that the scanning position of a scanner, which is a light scanning unit, has reached the acquisition start position IP1.

As the acquisition start position IP1 at that time, a position which makes it possible to determine that the drive has started is set relative to a position before the acquisition is started. Even while the scanner is in a halted state, an acquisition position varies by several μm. For this reason, the position to be set is determined, taking into account a positional variation value ΔE1 acquired at a stationary position relative to a drive start position SP1. For example, the positional variations of the scanner in a predetermined period of time are statistically processed to calculate ΔE1. The positional variation value ΔE1 is calculated on the basis of, for example, the mean value or dispersion of the positional variations of the scanner.

$$IP1=SP1+\Delta E1 \quad (3)$$

The scan is started, and the OCT scanner controller 311 detects that the current position has reached the acquisition start position IP1 and the acquisition by a line sensor is started. Using the method described above permits a reduced positional displacement of an acquired image without measuring the time delay before imaging an eye to be examined.

However, as described above, the value of a current position acquired by the OCT scanner controller 311 indicates the position of the scanner before an encoder acquisition time TE rather than an accurate current position. Accordingly, a disagreement may occur between a desired acquisition position and an actual acquisition position, and a reduction in the displacement of an acquired image may be less than that in the first embodiment. The method of the second embodiment should be used when the measurement of the time delay before a startup or image acquisition is skipped to shorten required time.

Third Embodiment

Figure 12A:
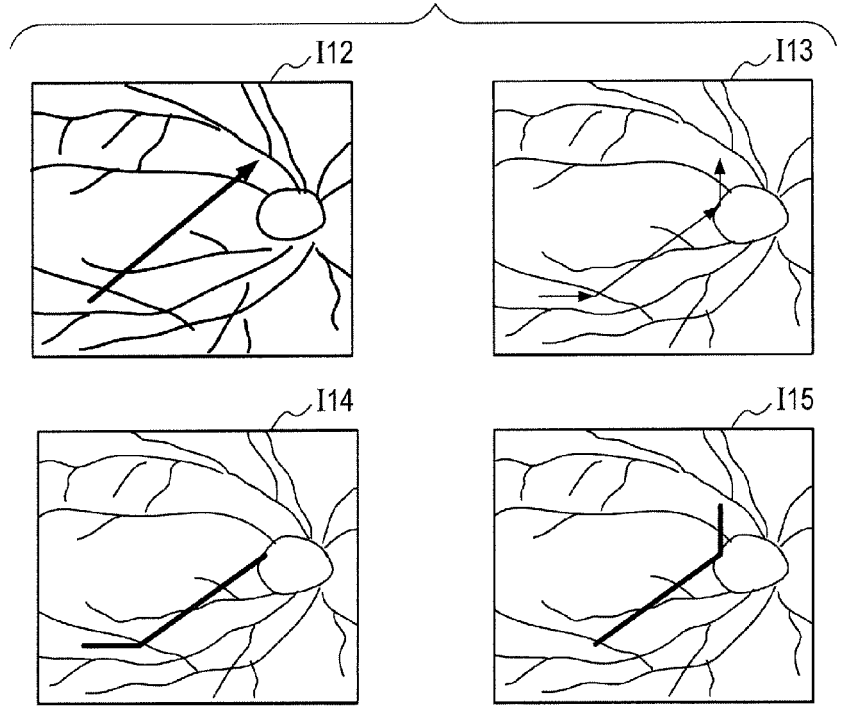
FIG. 12A illustrates the scanning trajectories of the measuring light in a third embodiment.

In the first and the second embodiments, the descriptions have been given of the examples in which only the scanner in one direction, namely, only one of the OCT-X scanner 113 and the OCT-Y scanner 112, is driven during the acquisition (i.e. during the acquisition of the light receiving signal). There is another case where she scanners in both directions, X and Y, are driven during the acquisition and a scan is carried out in a direction oblique to the X-direction and the Y-direction. Such examples include a vector scan in an oblique direction, a scan in which a reciprocal scan is repeated in the oblique direction to save time for shifting in the sub scanning direction during a reciprocal scan, and a radial scan in which the main scan is repeated while changing the angle, thus scanning in a radial pattern. The following will discuss a case where a scan is carried out in an oblique direction relative to the X-direction and the Y-direction. The scan pattern is indicated by a solid arrow I12 in FIG. 12A.

Figure 12B:
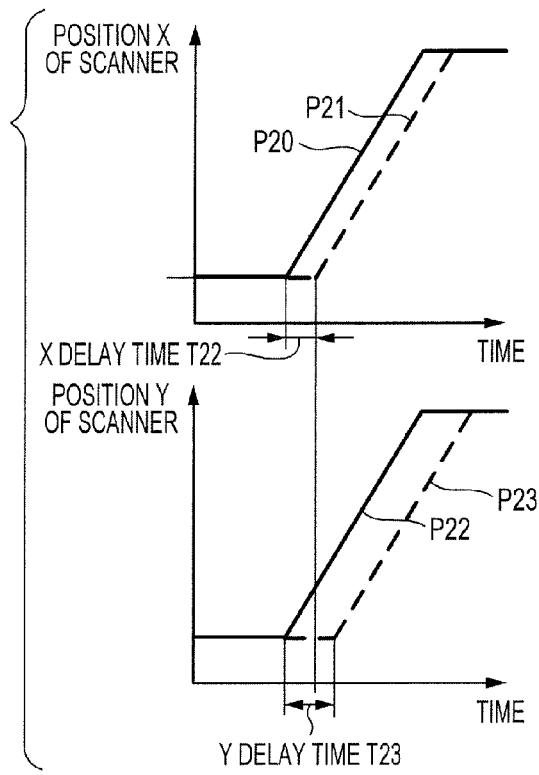
FIG. 12B illustrates the drive timings of the scanner.

At this time, both of an OCT-X scanner 113 and an OCT-Y scanner 112 are driven during the image acquisition, i.e. the acquisition of an image signal. The positional waveforms of the scanners will be as illustrated in FIG. 12B when the drive time delay of the OCT-Y scanner 112 is longer than the drive time delay of the OCT-X scanner 113. After the instruction is started, only the scanner in the X-direction is started to be driven first. After the elapse of the drive time delay of the scanner in the Y-direction, the both scanners in the X-direction and Y-direction are driven. Then, the scanner in the X-direction stops first, and the scanner in the Y-direction continues to be driven for a while before coming to a halt. Accordingly, if the drive time delays of the scanners in the X-direction and the Y-direction are different, then a scanning trajectory I13, which is different from a desired trajectory, will be obtained. At this time, if the time delay of the scanner in the X-direction is used as the waiting time, then an acquisition trajectory I14 will be obtained. Further, if the time delay of the scanner in the Y-direction is used as the waiting time, then an acquisition trajectory I15 will be obtained. Even if a desired acquisition trajectory is selected on the basis of a fundus observation image and a scan is performed, a resulting acquisition trajectory will be partly different from the desired trajectory. This may not only interfere with a diagnosis but lead to a misdiagnosis also.

Figure 12C:
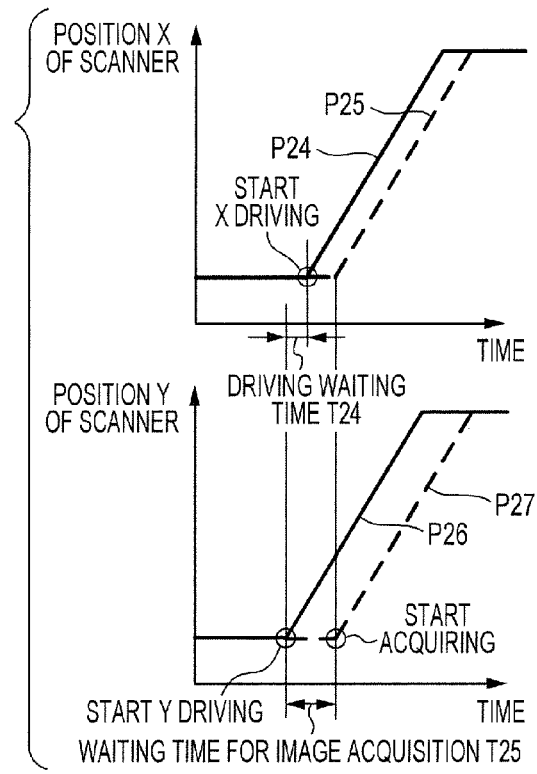
FIG. 12C illustrates the acquisition timing of the sensor.

Referring to FIG. 12B and FIG. 12C, a description will be given of a method that permits drive and image acquisition along a desired trajectory with a resultant reduced positional displacement of an acquired image even if the scanner in the X-direction and the scanner in the Y-direction have different drive time delays. First, according to the time delay measurement methods (I) and (II) in the first embodiment, the CPU 301 measures the drive time delays T22 and T23 of the scanner in the X direction and the scanner in the Y direction, respectively, prior to the image acquisition of an eye to be examined. Next, the CPU 301 compares the lengths of the time delays of the X scanner and the Y scanner and calculates the difference therebetween. Then, in the present embodiment, the CPU 301 determines that the scanner having a shorter time delay is the scanner in the X direction, and stores the difference in the time delay in a main memory unit 303 as drive waiting time T24 of the scanner in the X direction. The CPU 301 further stores a time delay T23 for driving the scanner in the Y-direction in the main memory unit 303 as acquisition start waiting time T25.

Referring now to FIG. 12C, a description will be given of an example of controlling a drive start timing and an acquisition start timing in the case where the drive time delay of the Y scanner is longer than the drive time delay of the X scanner as illustrated in FIG. 12B. First, the transmission of the drive instruction to the scanner in the Y-direction is started. Then, after the elapse of the drive waiting time T24 of the scanner in the X-direction, the drive of the scanner in the X-direction is started. Thus, both the scanners in the X-direction and the Y-direction actually start to be driven at the same timing, allowing both the scanners to be driven along a desired trajectory. Further, after the elapse of the acquisition start waiting time T25 since the drive of the scanner in the Y-direction was started, the acquisition is started.

The method described above permits drive and acquisition along a desired trajectory, thus making it possible to reduce a positional displacement of an acquired image, even if the scanner in the X-direction and the scanner in the Y-direction have different drive time delays.

Further, if the time delays of the scanners measured before the acquisition are significantly different from those at the time of shipment from a plant by magnitude that is greater than a degree caused by environmental or temperature influences, then the scanners may be faulty.

If the time delays have significantly changed, then other operating characteristics, such as the linearity of the scanners, may be faulty. A user has to be informed of the failure. However, when the method is applied, even if the time delays significantly change, the pixel displacement of an acquired image can be reduced, so that it is difficult to detect such a failure from an acquired image. Further, in the case of anomalies of other operating characteristics of the scanners, it is difficult to determine whether an acquired image indicates that the scanners are faulty or indicate a lesion of an eye to be examined.

Therefore, an arrangement may be made such that, if the time delays of the scanners measured before the acquisition have significantly changed from a predetermined range, i.e. out of the predetermined range, then the CPU 301 detects errors of the scanners. In this case, the CPU 301 causes a display unit 302 to display an error message to notify the user of a scanner failure. The predetermined period may be set, for example, by adding a margin to a time delay standard value for shipment, which takes individual differences into account. The margin may be determined on the basis of the amount of change obtained by environmental testing. In such a configuration, the CPU 301 and the display unit 302 correspond to an error notification unit that generates an error message.

Other Embodiments

In the foregoing embodiments, the descriptions have been given primarily of the measurement of the time delays of the scanners related to the OCT; however, the present invention is not limited thereto. For example, the present invention may be applied to a scanner related to the SLO.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (DC), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No 2014-084373, filed Apr. 16, 2014, which is hereby incorporated by reference herein in its entirety.

What is claimed is:

1. An ophthalmologic apparatus comprising:
    a light scanning unit that scans measuring light on an eye to be examined;
    an acquisition unit that acquires a light receiving signal from a light receiving unit that receives light reflected from the eye to be examined;
    an instruction unit that instructs a drive position of the light scanning unit;
    a position detection unit that detects a current position of the light scanning unit; and
    a measurement unit that measures a drive time delay from the moment the instruction unit issues an instruction to the moment the current position reaches the instructed drive position,
    wherein the acquisition unit starts acquiring the light receiving signal at timing based on the drive time delay.

2. The ophthalmologic apparatus according to claim 1, wherein
    the light scanning unit has a first light scanning unit, which scans measuring light on an eye to be examined, and a second light scanning unit, which scans the measuring light in a direction that is different from a direction of the first light scanning unit, and
    in the case where only one of the first scanning unit and the second scanning unit is driven while the light receiving signal is being acquired, the drive time delay on which the timing for starting the acquisition of the light receiving signal is based on is either the drive time delay of first light scanning unit or the drive time delay of the second light scanning unit whichever is driven during the acquisition.

3. The ophthalmologic apparatus according to claim 2, wherein the measurement unit measures the drive time delay at least when the ophthalmologic apparatus is started up, when the patient of the eye to be examined changes, when the eye to be examined is switched between right and left, or when the acquisition of the light receiving signal is started.

4. The ophthalmologic apparatus according to claim 2, comprising an error notification unit which generates an error message in the case where the drive time delay is out of a predetermined period.

5. The ophthalmologic apparatus according to claim 1, wherein
    the light scanning unit has a first light scanning unit, which scans measuring light on an eye to be examined, and a second light scanning unit, which scans the measuring light in a direction that is different from that of the first light scanning unit, and
    in the case where both the first scanning unit and the second scanning unit are driven while the light receiving signal is being acquired, the instruction unit delays timing for an instruction start to either the first light scanning unit or the second light scanning unit whichever has a shorter drive time delay from timing for an instruction start to the light scanning unit having the drive time delay that is longer, and
    the drive time delay on which the timing for starting the acquisition of the light receiving signal is the drive time delay of either the first light scanning unit or the second light scanning unit whichever has the longer drive time delay.

6. The ophthalmologic apparatus according to claim 5, wherein the measurement unit measures the drive time delay at least when the ophthalmologic apparatus is started up, when the patient of the eye to be examined changes, when the eye to be examined is switched between right and left, or when the acquisition of the light receiving signal is started.

7. The ophthalmologic apparatus according to claim 5, comprising an error notification unit which generates an error message in the case where the drive time delay is out of a predetermined period.

8. The ophthalmologic apparatus according to claim 1, wherein the measurement unit measures the drive time delay at least when the ophthalmologic apparatus is started up, when the patient of the eye to be examined changes, when the eye to be examined is switched between right and left, or when the acquisition of the light receiving signal is started.

9. The ophthalmologic apparatus according to claim 8, comprising an error notification unit which generates an error message in the case where the drive time delay is out of a predetermined period.

10. The ophthalmologic apparatus according to claim 1, comprising an error notification unit which generates an error message in the case where the drive time delay is out of a predetermined period.

11. An ophthalmologic apparatus comprising:
    a light scanning unit that scans measuring light on an eye to be examined;
    an acquisition unit that acquires a light receiving signal from a light receiving unit that receives light reflected from the eye to be examined; and
    an acquisition start position detection unit which detects that a scanning position of the light scanning unit has reached a predetermined position,
    wherein the acquisition unit starts the acquisition of the light receiving signal on the basis of timing detected by the position detection unit.

12. The ophthalmologic apparatus according to claim 11, wherein
    the light scanning unit has a first light scanning unit, which scans measuring light on an eye to be examined, and a second light scanning unit, which scans the measuring light in a direction that is different from a direction of the first light scanning unit, and
    in the case where only one of the first scanning unit and the second scanning unit is driven while the light receiving signal is being acquired, the light scanning unit to be detected by the position detection unit is either the first light scanning unit or the second light scanning unit whichever is driven during the acquisition.

* * * * *